(12) United States Patent
Terawaki et al.

(10) Patent No.: US 8,539,627 B2
(45) Date of Patent: Sep. 24, 2013

(54) BODY POSITION AND PRESSURE CONTROL APPARATUS

(75) Inventors: Masaki Terawaki, Komaki (JP); Takeaki Yoshikawa, Komaki (JP); Hiroaki Ito, Komaki (JP)

(73) Assignee: Tokai Rubber Industries, Ltd., Aichi-Ken (JP)

( * ) Notice: Subject to any disclaimer, the term of this patent is extended or adjusted under 35 U.S.C. 154(b) by 81 days.

(21) Appl. No.: 13/203,788

(22) PCT Filed: Dec. 20, 2010

(86) PCT No.: PCT/JP2010/072921
§ 371 (c)(1),
(2), (4) Date: Aug. 29, 2011

(87) PCT Pub. No.: WO2011/092970
PCT Pub. Date: Aug. 4, 2011

(65) Prior Publication Data
US 2011/0308019 A1    Dec. 22, 2011

(30) Foreign Application Priority Data
Jan. 27, 2010  (JP) .................................. 2010-015504

(51) Int. Cl.
*A61G 7/10*    (2006.01)
(52) U.S. Cl.
USPC ....................................... 5/713; 5/724; 5/727
(58) Field of Classification Search
USPC ............................................. 5/713, 724, 727
See application file for complete search history.

(56) References Cited

U.S. PATENT DOCUMENTS

| | | |
|---|---|---|
| 2004/0194220 A1 | 10/2004 | Price et al. |
| 2007/0094806 A1 | 5/2007 | Beretta |
| 2008/0097250 A1 | 4/2008 | Tochigi et al. |
| 2008/0183048 A1 | 7/2008 | Zhang |
| 2009/0054792 A1 | 2/2009 | Sato et al. |
| 2011/0064615 A1 | 3/2011 | Watanabe et al. |

FOREIGN PATENT DOCUMENTS

| | | |
|---|---|---|
| CN | 1893862 | 1/2007 |
| CN | 101234061 | 8/2008 |
| JP | 11-4856 | 1/1999 |
| JP | 11-004856 | 1/1999 |
| JP | 2000-189472 | 7/2000 |
| JP | 2002-528175 | 9/2002 |

(Continued)

OTHER PUBLICATIONS

Japan Office Action, dated Aug. 28, 2012 along with an English translation thereof.

(Continued)

*Primary Examiner* — Peter M Cuomo
*Assistant Examiner* — Brittany Wilson
(74) *Attorney, Agent, or Firm* — Greenblum & Bernstein P.L.C.

(57) ABSTRACT

A body position and pressure control apparatus is provided capable of highly accurately detecting body pressure distribution without causing a sense of discomfort for a sleeper, changing body positions, and distributing body pressure. The body position and pressure control apparatus has a mattress provided with a plurality of divided portions and supporting a sleeper, an elastomer sensor, and a body pressure adjuster controlling each of the divided portions based on an instruction from the elastomer sensor and thereby changing the body pressure distribution of the sleeper. The elastomer sensor has a sheet sensor main body and a calculator, the sensor main body having an elastomer sensor thin film, a plurality of electrodes, and a plurality of detectors corresponding to the divided portions provided between the electrodes.

9 Claims, 9 Drawing Sheets

(56) References Cited

FOREIGN PATENT DOCUMENTS

| | | |
|---|---|---|
| JP | 2005-160650 | 6/2005 |
| JP | 2005-204932 | 8/2005 |
| JP | 2006-129933 | 5/2006 |
| JP | 2006-320474 | 11/2006 |
| JP | 2008-178734 | 8/2008 |
| JP | 2009-281786 | 12/2009 |

OTHER PUBLICATIONS

China Office Action, with an English translation thereof.
Document "E," paragraphs [0008]-[0035]; and Figures 3-5, provides an English language translation for Document "h," line 1 in p. 2 through the last line in p. 4; and Figures 3-5.
Document "D," claim 1; paragraphs [0012]-[0018]; and Figure 1, provides an English language translation for Document "i," claim 1; line 15 in p. 2 through line 20 in p. 4; and Figure 1.

BODY POSITION AND PRESSURE CONTROL APPARATUS

TECHNICAL FIELD

The present invention relates to a body position and pressure control apparatus preventing bedsores for a bedridden person.

BACKGROUND TECHNOLOGY

A bedridden elderly person or patient cannot roll over as one wishes and mostly sleeps in the same position for a long time. Then, a portion where a bone projects and the body weight is concentrated is pressured, thus causing bad blood circulation and developing bedsores (pressure ulcers). To prevent bedsores, it is necessary to change body positions periodically to distribute the body pressure. It is a substantial burden, however, for a caregiver or nurse to change the body position of the bed-ridden elderly person or patient. It is thus difficult to rely solely on manpower for prevention of bedsores.

A variety of apparatuses have been proposed to prevent bedsores without manpower. For instance, Patent Literatures 1 and 2 each disclose a bedsore preventing apparatus having a mattress including a plurality of air bags, a pressure sensor corresponding to each of the air bags, and an air volume adjuster adjusting an air volume of the air bags. Furthermore, Patent Literature 3 discloses a mattress having a seat being a collection of a plurality of cells, a sensor disposed in each of the cells to detect a bedsore portion, and a controller adjusting an internal pressure of the cells.

RELATED ART

Patent Literatures

Patent Literature 1: Japanese Patent Application Publication No. 2002-528175
Patent Literature 2: Japanese Patent Laid-Open Publication No. 2000-189472
Patent Literature 3: Japanese Patent Laid-Open Publication No. 2006-320474

SUMMARY OF THE INVENTION

Shortcomings Resolved by the Invention

The bedsore preventing apparatus of Patent Literatures 1 and 2 above requires a pressure sensor to be disposed at each portion to detect body pressure. Each pressure sensor requires electrodes and wirings, thus inevitably increasing the number of electrodes and wirings and complicating the apparatus configuration. Furthermore, a sensor sheet including the pressure sensors is not soft and has poor stretchability. Thus, the sensor sheet placed on an upper surface of the mattress is difficult to fit along a body of a sleeper, thus causing a sense of discomfort for the sleeper. In the case where the body position is changed, the sensor sheet is difficult to follow the body movement. In addition, the sensor sheet is difficult to follow the movement of inflation and deflation of the air bags, thus deteriorating the detection accuracy of body pressure distribution.

The bedsore preventing apparatus of Patent Literatures 1 and 2 above prevents bedsores by inflating and deflating the air bags in the mattress so as to change the body position of the sleeper. Even if the body position of the sleeper is changed, however, the body is constantly in contact with the mattress. It is thus difficult to reduce the pressure exerted on a bone projection portion, and accordingly a bedsore prevention effect is not sufficient.

In view of the circumstances above, an object of the present invention is to provide a body position and pressure control apparatus capable of highly accurately detecting body pressure distribution without causing a sense of discomfort for a sleeper, changing body positions, and distributing body pressure.

Means for Resolving the Shortcomings (1) A body position and pressure control apparatus according to the present invention has a mattress having a plurality of divided portions and supporting a sleeper; an elastomer sensor having a sheet sensor main body and a calculator, the sensor main body being disposed one of above, below, and inside the mattress in a thickness direction thereof, having an elastomer sensor thin film, a plurality of electrodes connected to the sensor thin film, a plurality of detectors provided between the electrodes and corresponding to the divided portions, and being capable of outputting input load as electricity, the calculator calculating body pressure distribution of the sleeper from the output electricity; and a body pressure adjuster controlling each of the divided portions based on the body pressure distribution data detected by the elastomer sensor and thereby changing the body pressure distribution of the sleeper.

The body position and pressure control apparatus according to the present invention detects the body pressure distribution of the sleeper with the elastomer sensor. The elastomer sensor is provided with the sheet sensor main body having the sensor thin film composed of an elastomer. The term "composed of an elastomer" herein means that a base material of the sensor thin film is an elastomer. Thus, another component, such as, for example, a conductive filler, may be included other than the elastomer component.

The sensor main body is flexible and stretchable, thus easily fitting along the body of the sleeper. Even if the sensor main body is disposed proximate to the sleeper, for example, on the upper surface of the mattress, the sleeper hardly has a sense of discomfort, such as hardness and stiffness. In other words, the sleeper is hardly under any strain. In addition, the sensor main body easily follows the movement of the divided portions of the mattress and the body movement of the sleeper. The elastomer sensor can thus highly accurately detect the body pressure distribution.

The body pressure adjuster in the body position and pressure control apparatus of the present invention individually controls the divided portions of the mattress according to an instruction from the elastomer sensor based on the data of the body pressure distribution of the sleeper, and thereby changes the body pressure distribution of the sleeper. It is determined, for example, that the body pressure in a certain portion is high for a long period of time. Then, the internal pressure of the divided portions corresponding to the body portion may be reduced or the divided portions may be dented downward. Thereby, the body pressure in the portion can be reduced. Alternatively, the divided portions corresponding to other body portions may be projected upward so as to change the body position. Increasing the number of the divided portions relative to the sleeper, specifically, densely disposing small divided portions, can prevent an increase of the body pressure distributed in other portions, even if the body pressure in a particular portion is reduced by deflating the divided portions. Thus, the body position and pressure control apparatus according to the present invention can effectively prevent bedsores by distributing the body pressure or changing the body position of the sleeper.

(2) In the configuration (1) above, it is preferable that the divided portions are composed of bag portions filled with one of gas and liquid and that the body pressure adjuster supplies one of the gas and the liquid to the bag portions to inflate the bag portions and alternatively exhausts one of the gas and the liquid from the bag portions to deflate the bag portions, and thereby changes the body pressure distribution of the sleeper.

Inflating the bag portions pushes up a portion of the sleeper in contact with the bag portions. Thereby, the body pressure of the portion increases. Conversely, deflating the bag portions reduces the body pressure of a portion of the sleeper in contact with the bag portions. According to this configuration, merely increasing or decreasing the filler amount of the individual bag portions easily changes the body pressure distribution of the sleeper. Since gas or liquid is filled in the bag portions, the bag portions easily deform to fit along the body of the sleeper. Thus, the sleeper is hardly under any strain. Furthermore, using gas, such as air, as the filler can reduce the weight of the mattress.

(3) In the configuration (1) or (2) above, it is preferable that a breathable cushion mat disposed closer to the sleeper than the divided portions is further provided.

The elastomer sensor in the body position and pressure control apparatus according to the present invention has the sensor main body disposed above, below, or inside the mattress in the thickness direction thereof. The sensor main body has the elastomer sensor thin film, which has poor breathability. Humidity is thus likely to be trapped between the sensor main body and the sleeper, causing discomfort during sleep. In addition, the skin of the sleeper gets wet due to humidity, thus possibly likely to cause bedsores.

In this regard, the breathable cushion mat is provided between the sleeper and the divided portions according to this configuration. In the case where the sensor main body is disposed above the divided portions, for example, further placing the cushion mat on the sensor main body releases humidity trapped between the sleeper and the sensor main body. Furthermore, a sense of discomfort due to the placement of the sensor main body is reduced. Accordingly, the skin of the sleeper is prevented from being wet, and concurrently comfort during sleep is improved.

(4) In the configuration (3) above, it is preferable that the mattress has a cover member covering the divided portions; that the sensor main body and the cushion mat are stacked in sequence on the sleeper side of the divided portions inside the cover member; and that the sensor main body and the cushion mat are fixed to the cover member.

In order to accurately detect the body pressure distribution of the sleeper, it is preferable that the sensor main body is provided proximate to the sleeper. In the case where the sensor main body is placed on the upper surfaces of the divided portions, for example, the sensor main body may move or wrinkle according to the movement of the divided portions, thus possibly preventing accurate detection of the body pressure distribution of the sleeper.

According to this configuration, the sensor main body is fixed to the cover member of the mattress along with the cushion mat. Since the sensor main body is fixed in a state separated from the divided portions, the sensor main body is unlikely to move even if the divided portions move. Thus, the body pressure distribution of the sleeper can be detected accurately regardless of the movement of the divided portions. Furthermore, the sensor main body and the cushion mat are stacked in the sequence in the direction from the divided portions to the sleeper in this configuration. In other words, the cushion mat is placed on the sensor main body. Thus, humidity is unlikely to be trapped between the sleeper and the sensor main body. In addition, the sleeper hardly has a sense of discomfort due to the placement of the sensor main body.

(5) In the configuration (4) above, it is preferable that a sensor bag attachably/detachably fixed inside the cover member is further provided and that the sensor main body and the cushion mat are stored in the sensor bag.

The sensor main body and the cushion mat are stored in the attachable/detachable sensor bag, and thereby the sensor main body and the like can easily be removed together from the mattress. Thus, the sensor bag is removed from the mattress and the mattress is folded, and thereby the body position and pressure control apparatus of the present invention can be stored and packed compactly. It is also easy to clean the mattress.

(6) In the configuration (3) above, it is preferable that a sensor holder having the sensor main body and a pair of cushion mats fixed on two sides in a thickness direction of the sensor main body is further provided; that the mattress includes a cover member covering the divided portions; that the sensor holder is disposed on the sleeper side of the divided portions inside the cover member; and that the sensor holder is fixed to the cover member.

In this configuration, the sensor holder is disposed on the sleeper side of the divided portions. Specifically, the cushion mat, the sensor main body, and the cushion mat are stacked in the sequence in the direction from the divided portions to the sleeper. Since the cushion mats are provided on the both sides of the sensor main body, breathability and cushioning capability are improved.

Furthermore, the sensor holder is fixed to the cover member of the mattress. Namely, the sensor main body is fixed in a state separated from the divided portions, similar to the configuration (4) above. In addition, the cushion mat is provided between the sensor main body and the divided portions. Thus, the sensor main body does not come in contact with the divided portions. Accordingly, the movement of the sensor main body associated with the movement of the divided portions can further be prevented in this configuration. Thereby, the body pressure distribution of the sleeper can be accurately detected regardless of the movement of the divided portions.

(7) In the configuration (6) above, it is preferable that a sensor bag attachably/detachably fixed to the cover member is further provided and that the sensor holder is stored in the sensor bag.

The sensor holder is stored in the attachable/detachable sensor bag, and thereby the sensor holder can easily be removed from the mattress. Similar to the configuration (5) above, the sensor bag is removed from the mattress and the mattress is folded, and thereby the body position and pressure control apparatus of the present invention can be stored and packed compactly. It is also easy to clean the mattress.

(8) In any of the configurations (1) to (7) above, it is preferable that the sensor main body is provided with a plurality of ventilation holes penetrating in a thickness direction of the sensor thin film.

As described above, controlling humidity in the elastomer sensor is important to provide comfort during sleep and prevent bedsores for the sleeper. In this configuration, the plurality of ventilation holes penetrating in the thickness direction are provided in the sensor thin film. Thereby, the breathability of the sensor thin film, eventually the sensor main body, is enhanced. Thus, an increase in humidity between the sensor main body and the sleeper can be prevented.

(9) In any of the configurations (1) to (8) above, it is preferable that the divided portions are densely disposed in an area corresponding to a portion of the sleeper likely to cause bedsores.

Densely disposing the divided portions allows fine adjustment of body pressure. This configuration thus enables the body pressure in a portion likely to cause bedsores to be further finely adjusted, thereby effectively preventing bedsores. As described above, since small divided portions relative to the sleeper are densely disposed, the body pressure distributed to other portions can be prevented from increasing even if the body pressure in a particular portion is reduced by deflating the divided portions.

(10) In any of the configurations (1) to (9) above, it is preferable that the sensor main body has an elongation at break of 50% or greater.

In this configuration, the sensor main body has excellent stretchability. Thus, the following capability to the body of the sleeper is further improved and a sense of discomfort of the sleeper is further reduced. The durability of the sensor main body is also improved. In the present specification, elongation at break is measured in a method pursuant to JIS K 6251 (2004) and a dumbbell shape No. 5 is used as a test piece.

(11) In any of the configurations (1) to (10) above, it is preferable that, in the sensor main body, the electrodes include band-shaped front electrodes disposed on a front side of the sensor thin film and band-shaped rear electrodes disposed on a rear side of the sensor thin film; that the front electrodes and the rear electrodes intersect viewed from a front-rear direction to form detectors; and that electrostatic capacitance at the detectors is changed by input of the load.

In general, electrostatic capacitance (capacitance) of an electrostatic capacitance sensor provided with a dielectric film between a pair of electrodes can be obtained in the expression below (I)

$$C = \epsilon_0 \epsilon_r S/d \quad (I)$$

(C: Capacitance; $\epsilon_0$: Permittivity in vacuum; $\epsilon_r$: Relative permittivity of a dielectric film; S: Area of electrodes; d: Distance between electrodes)

For example, load is exerted on the sensor main body of this configuration, and then the sensor thin film (dielectric film) is compressed and is extended for the amount in a parallel direction relative to electrode surfaces. From the expression (I), the less the thickness of the sensor thin film is, or the distance between the electrodes d is, the greater the capacitance C of the detector is, the detector being provided between the front electrode and the rear electrode.

In this configuration, the front electrodes and the rear electrodes are both band shaped. The detectors are provided utilizing intersections of the front electrodes and the rear electrodes, thus reducing the number of electrodes and wirings. In addition, a variety of sensor main bodies can be configured having a different number and density of detectors by merely changing the number and placement of the front electrodes and the rear electrodes. Thus, a desired sensor main body can easily be configured according to divided portions.

(12) In any of the configurations (1) to (11) above, it is preferable that the front electrodes and the rear electrodes include an elastomer and a conductive filler filled in the elastomer.

In this configuration, the front electrodes and the rear electrodes can expand and contract along with the sensor thin film. Thus, it is unlikely that the front electrodes and the rear electrodes prevent the sensor thin film from expanding and contracting. Furthermore, the stretchability of the sensor main body further increases as a whole. Thus, the following capability to the body of the sleeper is further improved and a sense of discomfort of the sleeper is further reduced. The durability of the sensor main body is also improved.

DESCRIPTION OF THE NUMERICAL CHARACTERS

Figure 1:
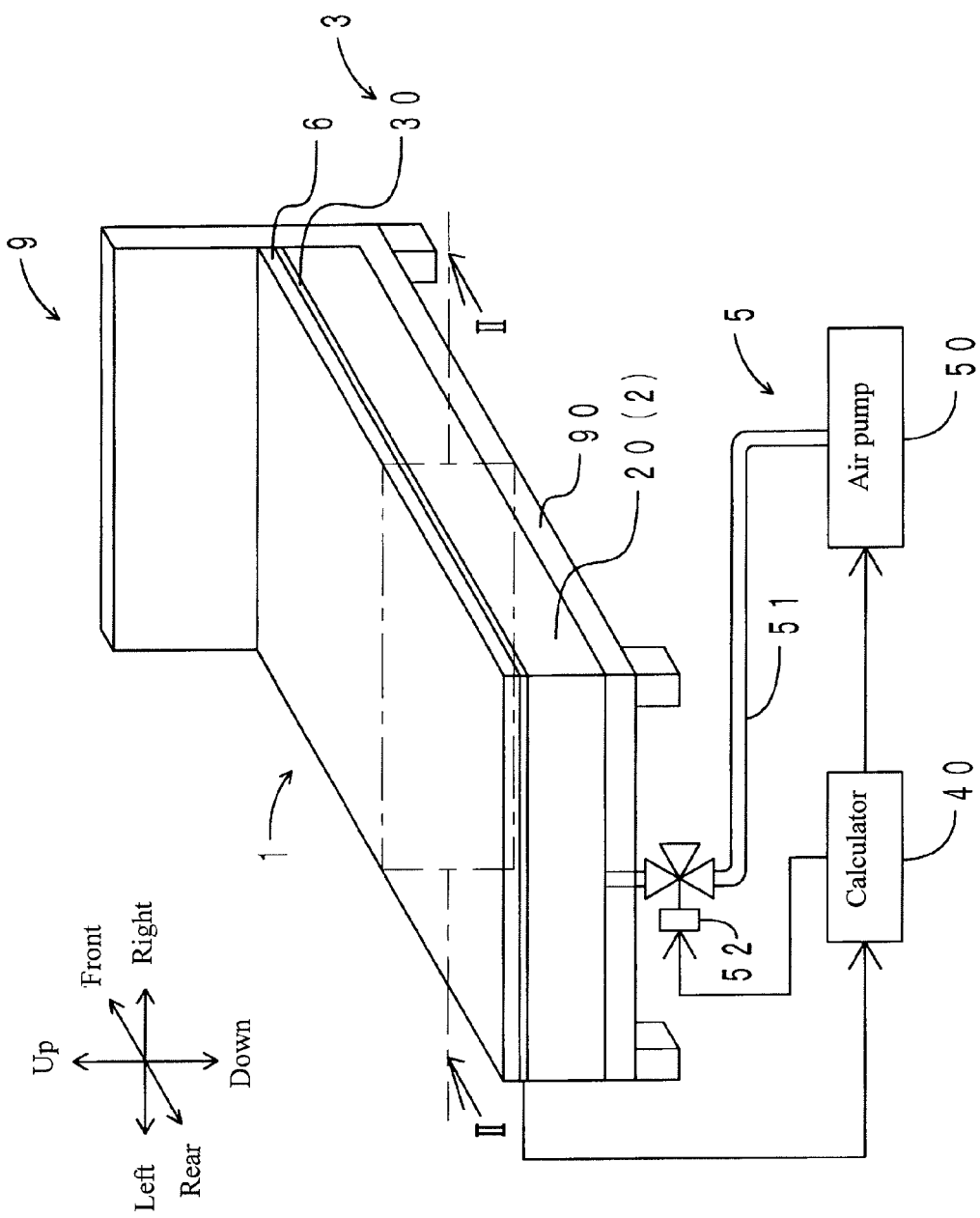
[FIG. 1] A schematic view of a body position and pressure control apparatus according to a first embodiment.

1: Body position and pressure control apparatus
2: Mattress; 20: Cover bag; 21: Air cell (bag portion); 210: Air supply outlet
22, 23, 25: Cover bag (Cover member); 24, 26: Sensor bag
3: Elastomer sensor; 30: Sensor main body; 31: Sensor thin film; 32: Front insulation coated layer
33: Rear insulation coated layer; 34: Front wiring connector; 35: Rear wiring connector
36: Board; 37: Sensor thin film; 38: Connector; 39: Wiring; 310: Ventilation hole
40: Calculator; 41: Power circuit; 42: CPU; 43: RAM; 44: ROM
45: Drive circuit
5: Air volume adjustment apparatus (Body pressure adjuster); 50: Air pump; 51: Hose; 52: Electromagnetic valve
6: Cushion mat
60: Sensor holder; 61, 62: Cushion mat
9: Bed; 91: Bed frame
01X-14X: Front electrode; 01Y-10Y: Rear electrode; 01x-14x: Front wiring
01y-10y: Rear wiring; A0101-A1410: Detector
01a-10a, 01b-10b, 01c-14c, 01d-14d: Electrode
S: Sleeper

EMBODIMENTS OF THE INVENTION

Embodiments of a body position and pressure control apparatus according to the present invention are explained below.

(First Embodiment)

[Configuration of Body position and pressure Control Apparatus]

Figure 2:
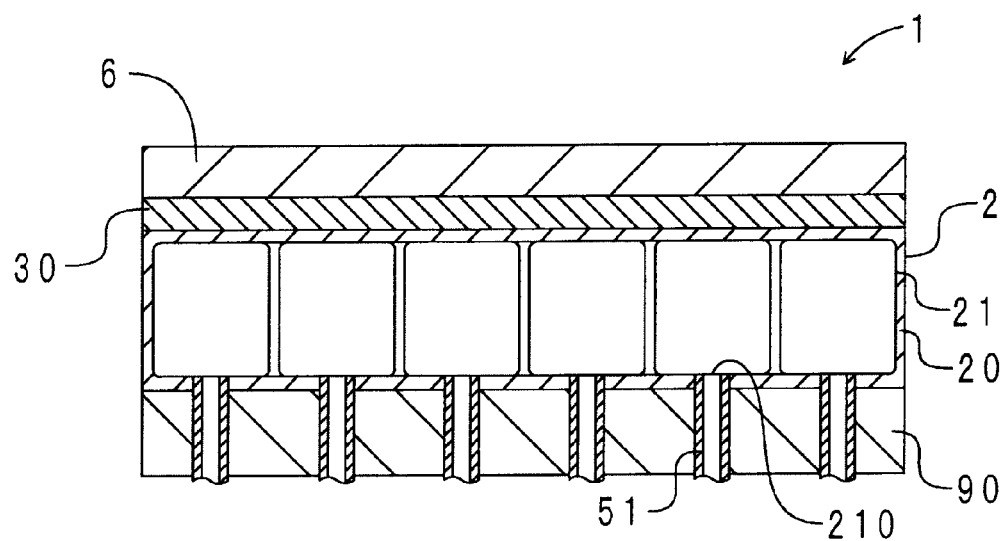
[FIG. 2] A cross-sectional view of FIG. 1 along line II-II.

A configuration of the body position and pressure control apparatus according to the present embodiment is first explained below. FIG. 1 is a schematic view of the body position and pressure control apparatus according to the present embodiment. FIG. 2 is a cross-sectional view of FIG. 1 along line II-II. As shown in FIGS. 1 and 2, the body position and pressure control apparatus 1 according to the present embodiment has a mattress 2, an elastomer sensor 3, an air volume adjustment apparatus 5, and a cushion mat 6.

Figure 5:
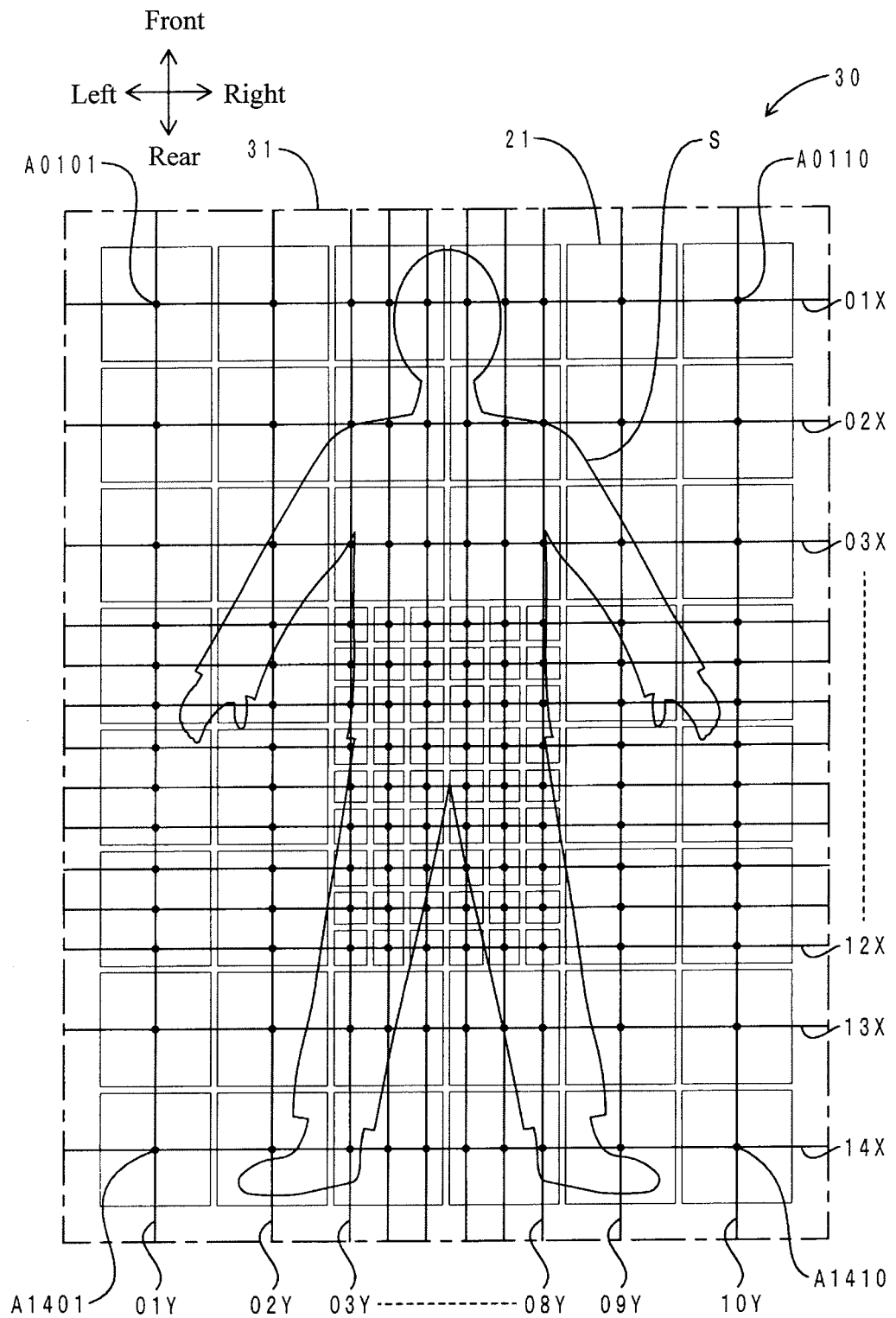
[FIG. 5] A transparent top view of the sensor main body and a mattress.

The mattress 2 is disposed on a bed frame 90 of a bed 9. The mattress 2 has a cover bag 20 and air cells 21. The cover bag 20 and the air cells 21 are both composed of a urethane film. The air cells 21 are stored inside the cover bag 20. As shown in FIG. 5 hereinafter described, a total of 96 air cells 21 are disposed. An air supply outlet 210 is provided in a lower surface of each of the air cells 21. A hose 51 of the air volume adjustment apparatus 5 is connected to the air supply outlet 210. The air cells 21 are included in bag portions of the present invention. A placement of the air cells 21 will be described hereinafter.

Figure 3:
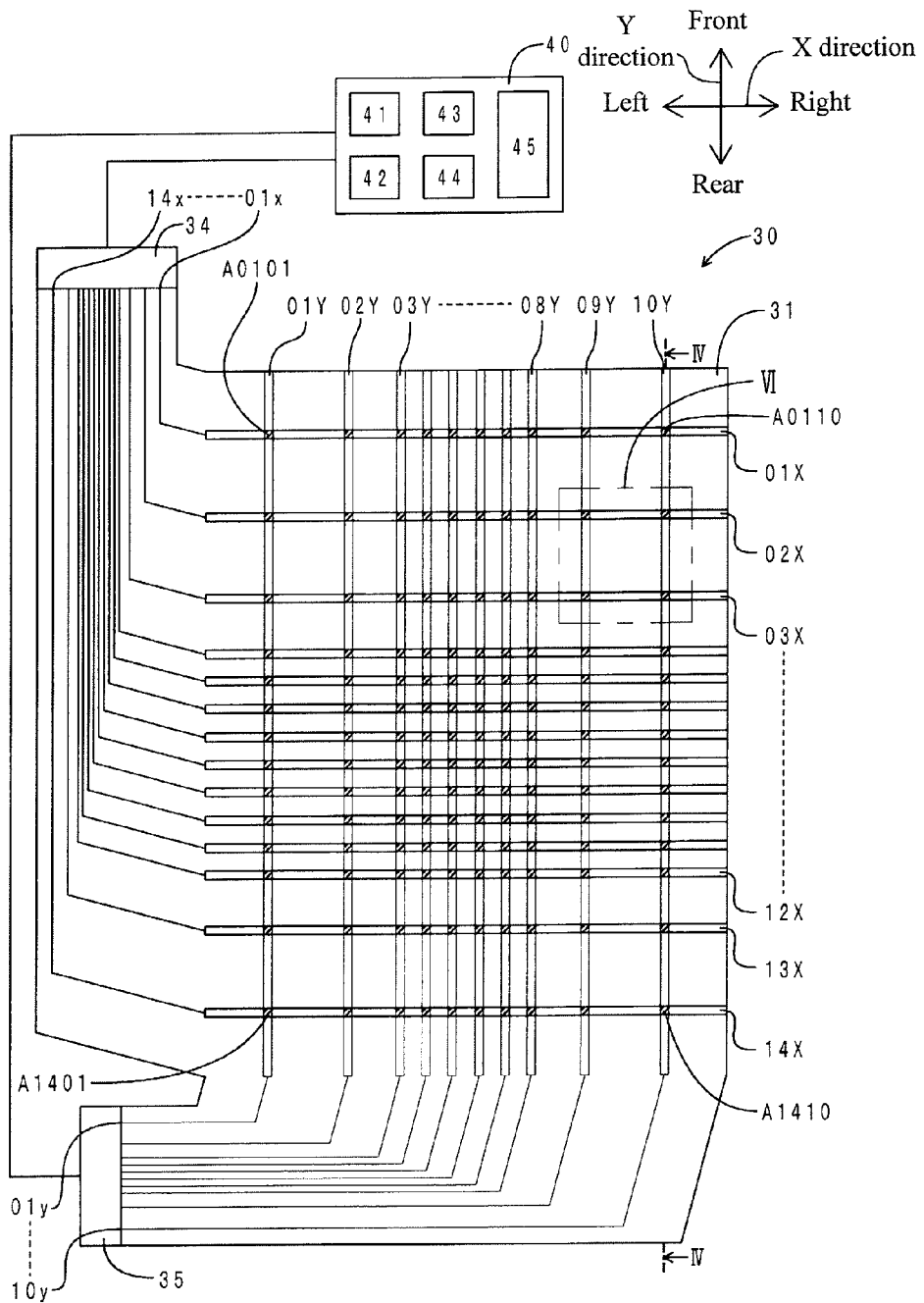
[FIG. 3] A transparent top view of a sensor main body.
Figure 4:
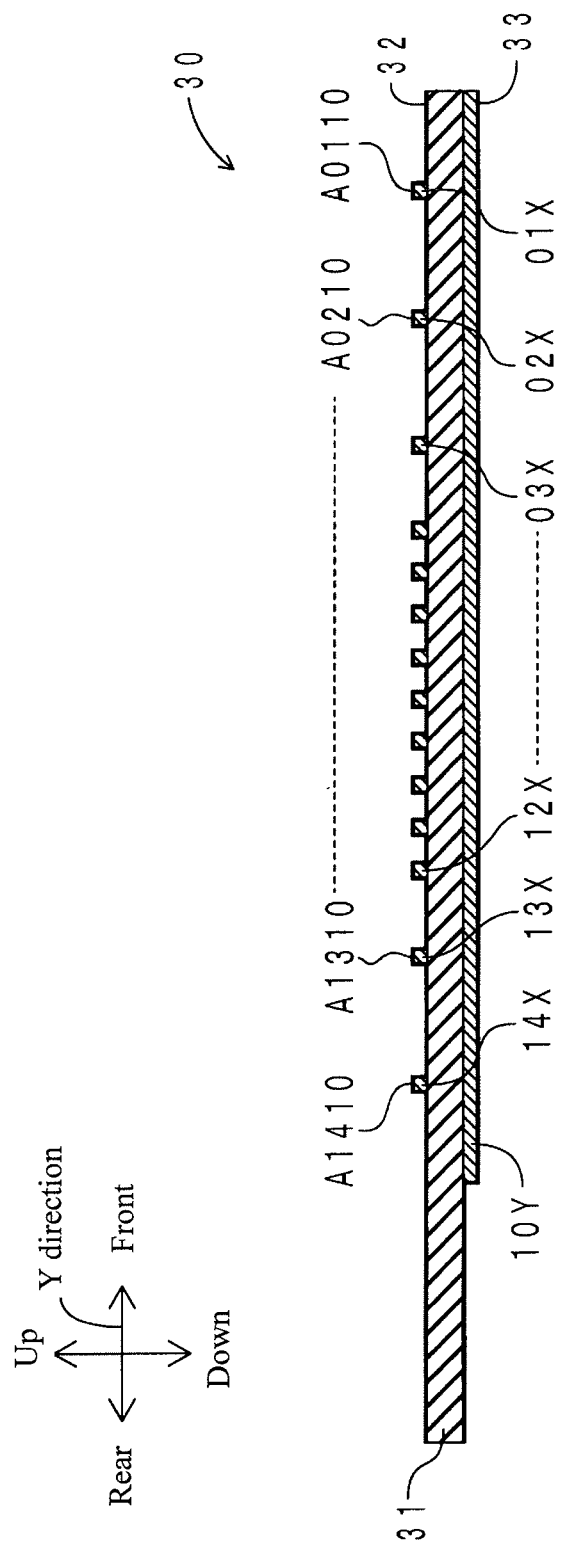
[FIG. 4] A cross-sectional view of FIG. 3 along line IV-IV.

The elastomer sensor 3 has a sensor main body 30 and a calculator 40. The sensor main body 30 is disposed on an upper surface of the mattress 2. A configuration of the sensor main body 30 is first explained. FIG. 3 is a transparent top view of the sensor main body. FIG. 4 is a cross-sectional view of FIG. 3 along line IV-IV. A front insulation coated layer and a rear insulation coated layer are omitted in FIG. 3. Rear electrodes and rear wirings are indicated by thin lines. A detector is indicated by a hatched portion.

As shown in FIGS. 3 and 4, the sensor main body 30 has a sensor thin film 31, front electrodes 01X to 14X, rear electrodes 01Y to 10Y, detectors A0101 to A1410, front wirings 01x to 14x, rear wirings 01y to 10y, front insulation coated layer 32, rear insulation coated layer 33, front wiring connector 34, and rear wiring connector 35. Of the reference numeral "Aaabb," the first two digits "aa" correspond to the front electrodes 01X to 14X and the last two digits "bb" correspond to the rear electrodes 01Y to 10Y. The sensor main body 30 has an elongation at break of 300%.

The sensor thin film 31 is a urethane rubber sheet. The sensor thin film 31 extends in X and Y directions (front-rear and left-right directions). The front-rear direction of the sensor thin film 31 corresponds to the vertical direction.

A total of 14 front electrodes 01X to 14X are disposed on an upper surface of the sensor thin film 31. The front electrodes 01X to 14X each include an acrylic rubber and a conductive carbon black. The front electrodes 01X to 14X each have a band shape and extend in the X direction (left-right direction). The front electrodes 01X to 14X are provided apart at a predetermined distance in the Y direction (front-rear direction) in substantially parallel to one another.

A total of 14 front wirings 01x to 14x are disposed on the upper surface of the sensor thin film 31. The front wirings 01x to 14x each include an acrylic rubber and silver powders. The front wirings 01x to 14x each have a linear shape. The front wiring connector 34 is disposed at the front left corner of the sensor thin film 31. The front wirings 01x to 14x connect left ends of the front electrodes 01X to 14X, respectively, and the front wiring connector 34.

The front insulation coated layer 32 is disposed on the sensor thin film 31. The front insulation coated layer 32 includes an acrylic rubber. The front insulation coated layer 32 has a sheet shape. The front insulation coated layer 32 covers from above the sensor thin film 31, the front electrodes 01X to 14X, and the front wirings 01x to 14x.

A total of 10 rear electrodes 01Y to 10Y are disposed on a lower surface of the sensor thin film 31. The rear electrodes 01Y to 10Y each include an acrylic rubber and a conductive carbon black. The rear electrodes 01Y to 10Y each have a band shape and extend in the Y direction. The rear electrodes 01Y to 10Y are provided apart at a predetermined distance in the X direction in substantially parallel to each other.

A total of 10 rear wirings 01y to 10y are disposed on the lower surface of the sensor thin film 31. The rear wirings 01y to 10y each include an acrylic rubber and silver powders. The rear wirings 01y to 10y each have a linear shape. The rear wiring connector 35 is disposed at the rear left corner of the sensor thin film 31. The rear wirings 01y to 10y connect rear ends of the rear electrodes 01Y to 10Y, respectively, and the rear wiring connector 35.

The rear insulation coated layer 33 is disposed below the sensor thin film 31. The rear insulation coated layer 33 includes an acrylic rubber. The rear insulation coated layer 33 has a sheet shape. The rear insulation coated layer 33 covers from below the sensor thin film 31, the rear electrodes 01Y to 10Y, and the rear wirings 01y to 10y.

As indicated with the hatched portions in FIG. 3, the detectors A0101 to A1410 are disposed at portions where the front electrodes 01X to 14X and the rear electrodes 01Y to 10Y intersect (overlap) vertically. The detectors A0101 to A1410 are each provided with a portion of the front electrodes 01X to 14X, a portion of the rear electrodes 01Y to 10Y, and a portion of the sensor thin film 31. A total of 140 (14×10) detectors A0101 to A1410 are disposed across a substantially entire surface of the sensor main body 30. Furthermore, the detectors A0101 to A1410 are densely disposed in an area corresponding to the lower back of a sleeper (central area).

The placement of the detectors A0101 to A1410 and the air cells 21 of the mattress 2 is explained. FIG. 5 is a transparent top view of the sensor main body and the mattress. For explanation purposes, the components other than the front electrodes, the rear electrodes, the detectors, and the air cells are omitted in FIG. 5. The external edge of the sensor thin film is indicated by a dashed-dotted line. The front electrodes and the rear electrodes are indicated by a solid line. The transparently visible air cells are indicated by a thin line.

As shown in FIG. 5, one air cell 21 is disposed every three detectors A0103 to A0308 and A1303 to A1408 adjacent in the left-right direction. One air cell 21 is disposed every three detectors A0401 to A1202 and A0409 to A1210 adjacent in the front-rear direction. For other detectors, one air cell 21 is provided to one detector.

The detectors A0403 to A1208 are disposed in the vicinity of the lower back of a sleeper S. Distances in the up-down and left-right directions between the detectors A0403 to A1208 are narrower than those between the detectors disposed in the remaining area. In other words, the detectors A0403 to A1208 are densely disposed. The air cells 21 corresponding to the detectors A0403 to A1208 are smaller than those in the remaining area. A sacrum is located in the lower back of the sleeper S. The lower back is one of the bone projection portions, which are likely to develop bedsores. Thus, the air cells 21 are densely disposed in portions likely to develop bedsores.

A configuration of the calculator 40 is explained below. As shown in FIG. 3, the calculator 40 is electrically connected to the front wiring connector 34 and rear wiring connector 35 of the sensor main body 30.

The calculator 40 has a power circuit 41, a CPU (Central Processing Unit) 42, a RAM (Random Access Memory) 43, a ROM (Read Only Memory) 44, and a drive circuit 45.

The power circuit 41 applies a sinusoidal alternating voltage to the detectors A0101 to A1410. The ROM 44 stores in advance a map that indicates a correspondence between capacitance and load (body pressure) in the detectors A0101 to A1410. The ROM 44 also stores a threshold value of the body pressure. The RAM 43 temporarily stores an impedance and a phase input from the front wiring connector 34 and the rear wiring connector 35. The CPU 42 retrieves the capacitance of the detectors A0101 to A1410 based on the impedance and phase stored in the RAM 43, and then calculates body pressure distribution in the sensor main body 30 from the capacitance. The drive circuit 45 is connected to an air pump 50 and an electromagnetic valve 52 of the air volume adjustment apparatus 5 hereinafter described.

Referring back to FIG. 1, the air volume adjustment apparatus 5 has the air pump 50, the hose 51, and the electromagnetic valve 52. The air volume adjustment apparatus 5 is included in a body pressure adjuster of the present invention. The air pump 50 is connected to the calculator 40 and the drive circuit 45. The air pump 50 is connected to each of the air cells 21 of the mattress 2 by way of the hose 51 and the electromagnetic valve 52. In FIG. 1, only one hose 51 and one electromagnetic valve 52 are indicated between the air pump 50 and the air cells 21 for explanation purposes. The electromagnetic valve 52 is a three-way valve, of which one way is open to the air.

In response to an instruction to supply air from the calculator 40, two ways of the electromagnetic valve 52 are opened and air is supplied from the air pump 50 to the air cell 21. In response to an instruction to exhaust air from the calculator 40, one way open to the air of the electromagnetic valve 52 is opened and air is exhausted from the air cell 21.

The cushion mat 6 is a three-dimensional fabric composed of polyethylene terephthalate and the like ("Fusion (registered trademark)" of Asahi Kasei Fibers Corp.). The cushion mat 6 is disposed on the upper surface of the sensor main body 30.

[Movement of Body Position and Pressure Control Apparatus]

The movement of the body position and pressure control apparatus 1 is explained below. Before the sleeper S lies down on the body position and pressure control apparatus 1, the capacitance C is first calculated at each of the detectors A0101 to A1410. Specifically, the capacitance C is calculated in scanning of the detector A010 to the detector A1410. The calculated capacitance C is stored in the RAM 43 for each of the detectors A0101 to A1410.

After the sleeper S lies down on the body position and pressure control apparatus 1, the capacitance C is calculated at each of the detectors A0101 to A1410. The calculated capacitance C is stored in the RAM 43 for each of the detectors A0101 to A1410. From a change amount $\Delta C$ of the capacitance C before and after the sleeper S lies down, the CPU 42 calculates the body pressure distribution in the sensor main body 30. Specifically, the capacitance C is substituted to the capacitance-body pressure map previously stored in the ROM 44, and then the body pressure is calculated for any detectors A0101 to A1410.

The calculated body pressure data are stored in the RAM 43 for a predetermined period of time. The CPU 42 compares the body pressure data with the threshold value stored in the ROM 44. If the CPU 42 determines that the body pressure above the threshold value continues for a predetermined period of time, the CPU 42 causes the drive circuit 45 to drive the air volume adjustment apparatus 5. Specifically, the electromagnetic valve 52 of the air cell 21 corresponding to an area of high body pressure is opened so as to exhaust air. Then, the air cell 21 deflates. Thereby, the body pressure in the area can be reduced. Conversely, the electromagnetic valve 52 of the air cell 21 corresponding to an area of low body pressure is opened to supply air from the air pump 50. Then, the air cell 21 inflates. Thus, the body pressure can be distributed and the body position can be changed.

[Functions and Effects]

Functions and effects of the body position and pressure control apparatus 1 of the present embodiment is explained below. The body position and pressure control apparatus 1 of the present embodiment uses the elastomer sensor 3 to detect the body pressure distribution of the sleeper S. Specifically, the sleeper S lies down on the sheet-type sensor main body 30 with the cushion mat 6 therebetween. The sensor main body 30 has the sensor thin film 31 composed of a urethane rubber. The front electrodes 01X to 14X and the rear electrodes 01Y to 10Y are also composed of an elastomer. Thus, it is unlikely that the front electrodes 01X to 14X and the rear electrodes 01Y to 10Y restrict expansion and contraction of the sensor thin film 31. The sensor main body 30, which is soft and stretchable, easily fits along the body of the sleeper S. Furthermore, the sleeper S hardly has a sense of discomfort, such as hardness and stiffness. In other words, the sleeper S is hardly under any strain. In addition, the sensor main body 30 has high following capability to the movement of the air cells 21 and the body movement of the sleeper S. The body position and pressure control apparatus 1 of the present embodiment can thus highly accurately detect the body pressure distribution. The sensor main body 30 also has high durability.

The front electrodes 01X to 14X and the rear electrodes 01Y to 10Y included in the sensor main body 30 each have a band shape. The detectors A0101 to A1410 are provided utilizing the intersections of the front electrodes 01X to 14X and the rear electrodes 01Y to 10Y, thus reducing the number of electrodes and wirings. Specifically, a total of 140 detectors A0101 to A1410 are provided in the sensor main body 30. To provide electrodes to each of the detectors A0101 to A1410, 140 front electrodes and 140 rear electrodes are required. The sensor main body 30 of the present embodiment, however, requires only a total of 24 (14+10) front electrodes 01X to 14X and rear electrodes 01Y to 10Y to secure 140 detectors A0101 to A1410, thus reducing the number of disposed electrodes and wirings. In addition, the number and density of the detectors can be adjusted only by changing the number and placement of the front electrodes and the rear electrodes. It is thus easy to configure a desired sensor main body according to the number and size of the air cells 21.

The body position and pressure control apparatus 1 of the present embodiment has the mattress 2 provided with the numerous air cells 21 as divided portions. Thus, the body pressure of the sleeper S can easily be distributed or the body position can be changed by supplying or exhausting air to or from the air cells 21. Accordingly, bedsores can effectively be prevented for bedridden elderly persons or patients. Furthermore, the air cells 21, which are filled with air, easily deform along the body of the sleeper S, thus hardly causing any strain on the sleeper S. Compared with the case of using liquid, the weight of the mattress 2 is light.

The air cells 21 are most densely disposed in the vicinity of the lower back of the sleeper S. Similarly, the detectors A0403 to A1208 of the sensor main body 30 are also most densely disposed in the vicinity of the lower back of the sleeper S. The lower back is one of the portions where bedsores are likely to develop. The body position and pressure control apparatus 1 of the present embodiment can highly accurately detect the body pressure distribution in the vicinity of the lower back and finely adjust the body pressure in the vicinity of the lower back, thereby effectively preventing bedsores. Furthermore, the air cells 21 disposed in the vicinity of the lower back are smaller than the air cells 21 disposed in the remaining area. Even if the body pressure is reduced in the vicinity of the lower back by deflating specific air cells 21, the body pressure distributed in other portions can thus be prevented from increasing.

In the body position and pressure control apparatus 1 of the present embodiment, the cushion mat 6 is disposed on the upper surface of the sensor main body 30. In other words, the cushion mat 6 is provided between the sleeper S and the sensor main body 30. The cushion mat 6 has high breathability. Humidity is thus unlikely to be trapped between the sensor main body 30 and the sleeper S, thereby preventing bedsores and improving comfort during sleep.

(Second Embodiment)

A body position and pressure control apparatus of the present embodiment is different from the body position and pressure control apparatus of the first embodiment mainly in a configuration of a sensor main body. Thus, only the difference is explained herein.

Figure 6:
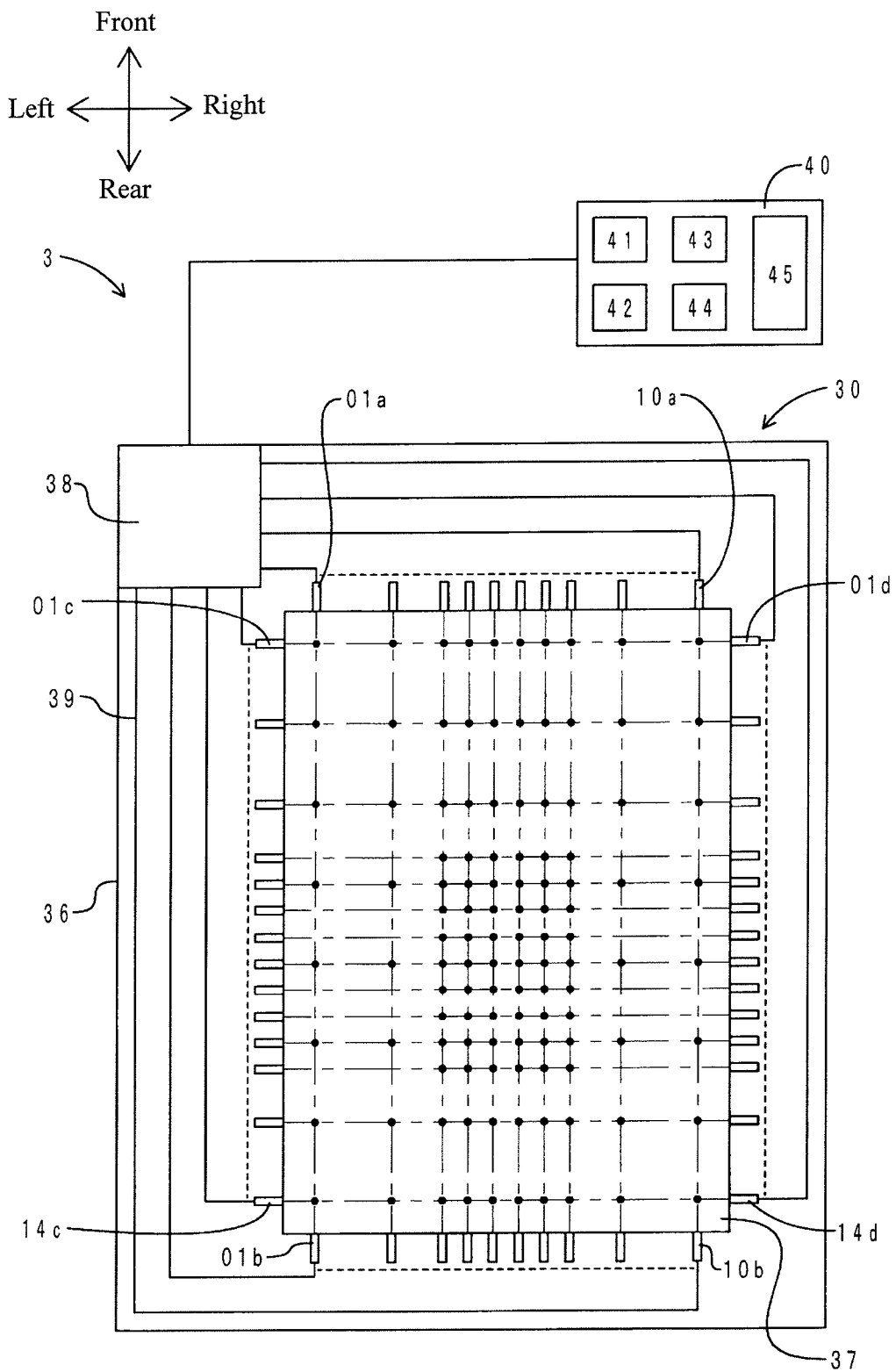
[FIG. 6] A top view of a sensor main body of a body position and pressure control apparatus according to a second embodiment.

FIG. 6 is a top view of the sensor main body of the body position and pressure control apparatus according to the present embodiment. In FIG. 6, components corresponding to those in FIG. 3 are represented by the same reference numerals. For explanation purposes, a wiring is partially omitted in FIG. 6.

As shown in FIG. 6, a sensor main body 30 has a board 36; a sensor thin film 37; a connector 38; electrodes 01*a* to 10*a*, 01*b* to 10*b*, 01*c* to 14*c*, and 01*d* to 14*d*; and a wiring 39.

The board 36, which is composed of an elastomer, has a rectangular plate shape. The board 36 is elastically deformable. The sensor thin film 37 is disposed on an upper surface of the board 36. The sensor thin film 37, which is composed of an ethylene-propylene-diene terpolymer (EPDM) mixed with a conductive filler, has a rectangular plate shape. The sensor thin film 37 contains the conductive filler at a ratio of approximately 45 vol % relative to 100 vol % of a volume of the sensor thin film 37. In a state where no load is input (no-load state), the sensor thin film 37 has high conductivity. With the load exerted, the sensor thin film 37 deforms and causes a change in a contact state of the conductive filler. Then, a three-dimensional conductive path collapses, thus increasing the electric resistance of the sensor thin film 37. Thus, the electric resistance of the sensor thin film 37 increases in accordance with an increase in an amount of elastic deformation. The connector 38 has a square plate shape. The connector 38 is disposed at a front left corner of the upper surface of the board 36.

The electrodes 01*a* to 10*a* are arrayed on a front side of the sensor thin film 37 with a predetermined distance apart therebetween. The electrodes 01*b* to 10*b* are arrayed on a rear side of the sensor thin film 37 with a predetermined distance apart therebetween. The electrodes 01*a* to 10*a* and the electrodes 01*b* to 10*b* are opposed to each other in the front-rear direction as shown with dashed-dotted lines in FIG. 6.

The electrodes 01*c* to 14*c* are arrayed on a left side of the sensor thin film 37 with a predetermined distance apart therebetween. The electrodes 01*d* to 14*d* are arrayed on a right side of the sensor thin film 37 with a predetermined distance apart therebetween. The electrodes 01*c* to 14*c* and the electrodes 01*d* to 14*d* are opposed to each other in the left-right direction as shown with dashed-dotted lines in FIG. 6. Intersections of the dashed-dotted lines (a total of 140=14×10) are detectors.

The electrodes 01*a* to 10*a*, 01*b* to 10*b*, 01*c* to 14*c*, and 01*d* to 14*d* and the connector 38 are each connected by the wiring 39.

A calculator 40 is electrically connected to the connector 38. A ROM 44 stores in advance a map that indicates a correspondence between capacitance and load (body pressure) in the detectors. The ROM 44 also stores a threshold value of the body pressure. A power circuit 41 applies a direct voltage to the detectors. The direct voltage is applied to the total of 140 detectors sequentially in a scanning manner. The electric resistance of each of the detectors is temporarily stored in a RAM 43. A CPU 42 calculates load distribution of the sensor thin film 37 from the electric resistance stored in the RAM 43. A drive circuit 45 is connected to an air pump 50 and an electromagnetic valve 52 in aforementioned FIG. 1.

The body position and pressure control apparatus of the present embodiment has similar functions and effects to the body position and pressure control apparatus of the first embodiment with respect to the components having common configurations. Furthermore, the body position and pressure control apparatus of the present embodiment can calculate body pressure distribution from a change in the electric resistance of the sensor main body 30.

(Third Embodiment)

A body position and pressure control apparatus of the present embodiment is different from the body position and pressure control apparatus of the first embodiment in that ventilation holes are provided in a sensor thin film. Thus, only the difference is explained herein.

Figure 7:
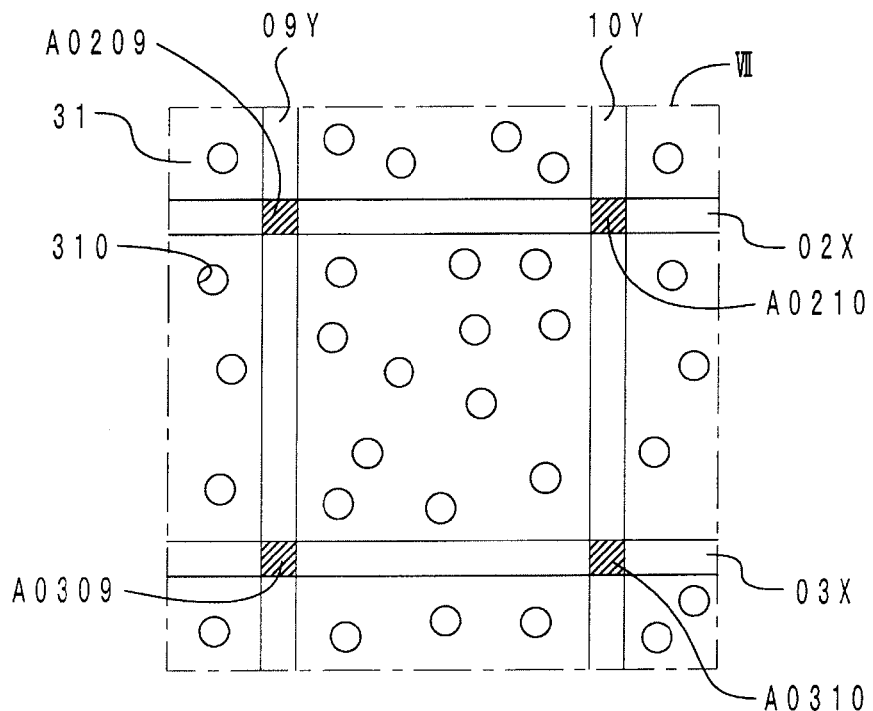
[FIG. 7] An enlarged view of a portion corresponding to an area surrounded by a dashed-dotted line in FIG. 3 in a sensor main body of a body position and pressure control apparatus according to a third embodiment.

FIG. 7 is an enlarged view of a portion corresponding to an area surrounded by a dashed-dotted line in FIG. 3 in a sensor main body of the body position and pressure control apparatus according to the present embodiment. For explanation purposes, the size of the ventilation holes is emphasized in FIG. 7. In FIG. 7, components corresponding to those in FIG. 3 are represented by the same reference numerals. As shown in FIG. 7, a plurality of ventilation holes 310 are provided in a sensor thin film 31. The ventilation holes 310 penetrate in the thickness direction of the sensor thin film 31. The ventilation holes 310 are disposed so as to avoid front electrodes 01X to 14X and rear electrodes 01Y to 10Y.

The body position and pressure control apparatus of the present embodiment has similar functions and effects to the body position and pressure control apparatus of the first embodiment with respect to the components having common configurations. In the body position and pressure control apparatus of the present embodiment, the sensor thin film 31, namely, the sensor main body 30, is breathable. Thus, humidity is unlikely to be trapped between the sensor main body 30 and a sleeper S, thereby improving comfort during sleep for the sleeper and enhancing bedsore prevention effects.

(Fourth Embodiment)

A body position and pressure control apparatus of the present embodiment is different from the body position and pressure control apparatus of the first embodiment in that a sensor main body and a cushion mat are provided inside a mattress. Thus, only the difference is explained herein.

Figure 8:
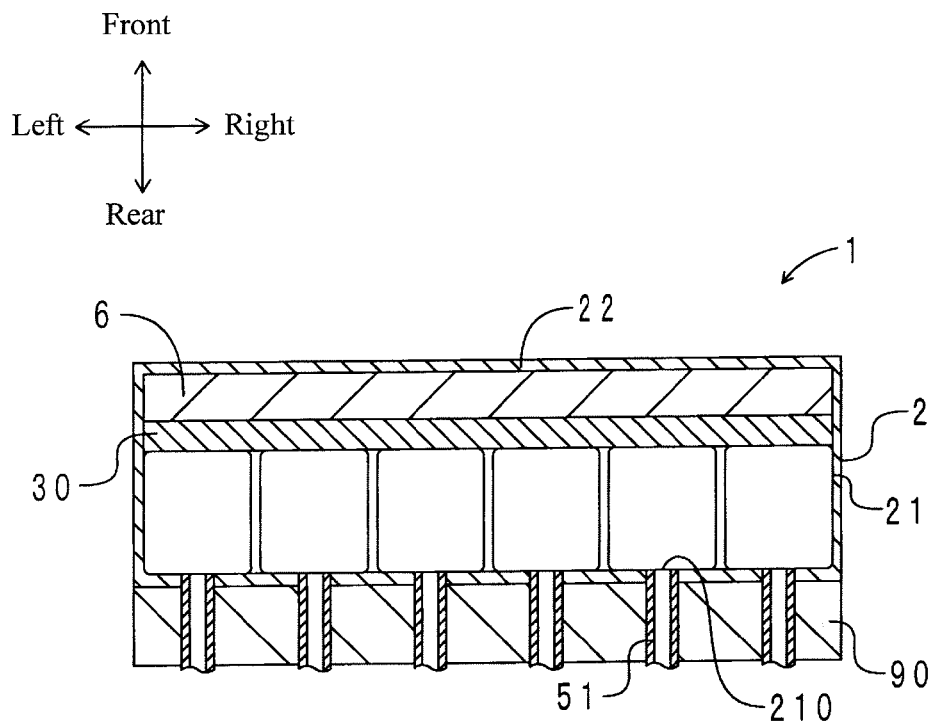
[FIG. 8] A cross-sectional view of a body position and pressure control apparatus according to a fourth embodiment.

FIG. 8 is a cross-sectional view of the body position and pressure control apparatus according to the present embodiment. FIG. 8 corresponds to FIG. 2. In FIG. 8, components corresponding to those in FIG. 2 are thus represented by the same reference numerals. As shown in FIG. 8, in a body position and pressure control apparatus 1 of the present embodiment, a sensor main body 30 and a cushion mat 6 are disposed inside a mattress 2.

The mattress 2 is provided with air cells 21 and a cover bag 22. The air cells 21 and the cover bag 22 are both composed of a urethane film. The air cells 21 are stored inside the cover bag 22 and is disposed in a lower portion of the cover bag 22. An air supply outlet 210 is provided to a lower surface of each of the air cells 21. A hose 51 of an air volume adjustment apparatus 5 is connected to the air supply outlet 210. The cover bag 22 is included in a cover member of the present invention.

A sensor main body 30 is stored inside the cover bag 22. The sensor main body 30 is disposed on upper surfaces of the air cells 21. The sensor main body 30 and the air cells 21 are not fixed. A configuration of the sensor main body 30 is identical to that in the first embodiment.

The cushion mat 6 is disposed on an upper surface of the sensor main body 30. The cushion mat 6 is bonded to a periphery of the sensor main body 30. An upper surface of the cushion mat 6 is bonded to an internal surface of an upper skin of the cover bag 22. Thus, the sensor main body 30 is fixed to the cover bag 22 through the cushion mat 6.

The body position and pressure control apparatus of the present embodiment has similar functions and effects to the body position and pressure control apparatus of the first embodiment with respect to the components having common configurations. In the body position and pressure control apparatus 1 of the present embodiment, the sensor main body 30 is fixed to the cover bag 22 of the mattress 2 along with the cushion mat 6. The sensor main body 30, however, is not fixed to the air cells 21. Since the sensor main body 30 is fixed in a state separated from the air cells 21, the sensor main body 30 is unlikely to move even if the air cells 21 move. Thus, body pressure distribution of a sleeper can be accurately detected regardless of the movement of the air cells 21.

(Fifth Embodiment)

A body position and pressure control apparatus of the present embodiment is different from the body position and pressure control apparatus of the fourth embodiment in that a sensor main body and a cushion mat are provided inside a sensor bag. Thus, only the difference is explained herein.

Figure 9:
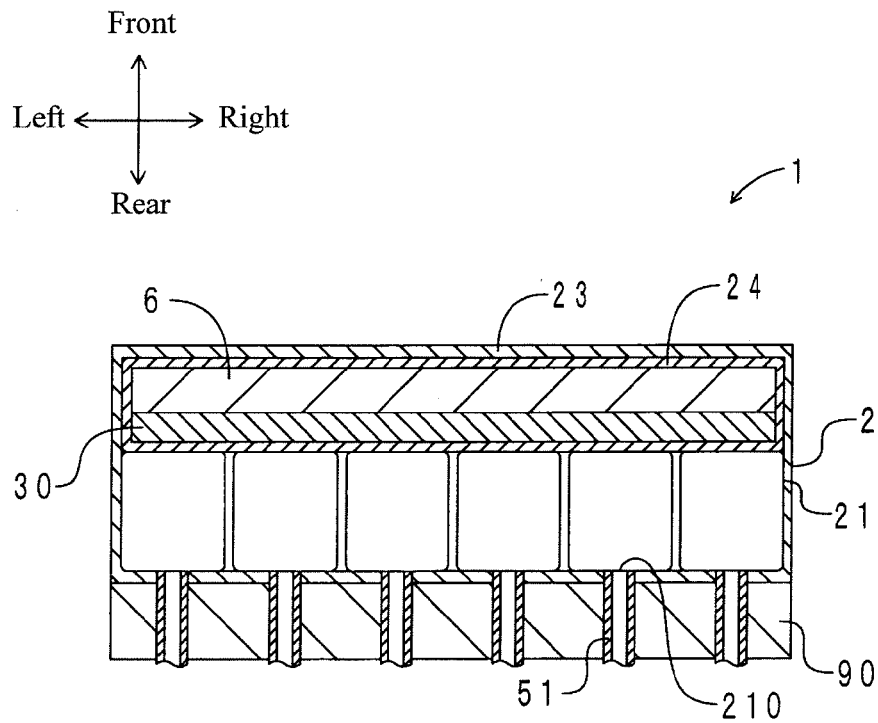
[FIG. 9] A cross-sectional view of a body position and pressure control apparatus according to a fifth embodiment.

FIG. 9 is a cross-sectional view of the body position and pressure control apparatus according to the present embodiment. FIG. 9 corresponds to FIG. 8. In FIG. 9, components corresponding to those in FIG. 8 are thus represented by the same reference numerals. As shown in FIG. 9, a body position and pressure control apparatus 1 of the present embodiment has a mattress 2, a sensor bag 24, a sensor main body 30, and a cushion mat 6.

The mattress 2 is provided with air cells 21 and a cover bag 23. The air cells 21 are stored inside the cover bag 23 and is disposed in a lower portion of the cover bag 23. A plurality of snap buttons (not shown in the drawing) to attach a sensor bag 24 are provided along a periphery of an internal surface of an upper skin of the cover bag 23. The cover bag 23 is included in a cover member of the present invention.

The sensor bag 24 is stored inside the cover bag 23 and is disposed above the air cells 21. A plurality of snap buttons (not shown in the drawing) are provided along a periphery of an upper surface of the sensor bag 24. The snap buttons of the cover bag 23 and the snap buttons of the sensor bag 24 are engaged, and thereby the sensor bag 24 is detachably attached to the cover bag 23.

The sensor main body 30 and the cushion mat 6 are stored inside the sensor bag 24. The cushion mat 6 is disposed on an upper surface of the sensor main body 30 and is bonded to a periphery of the sensor main body 30. The sensor main body 30 and the cushion mat 6 are fixed to the cover bag 23 through the sensor bag 24.

The body position and pressure control apparatus of the present embodiment has similar functions and effects to the body position and pressure control apparatus of the fourth embodiment with respect to the components having common configurations. In the body position and pressure control apparatus 1 of the present embodiment, the sensor main body 30 and the cushion bag 6 are fixed to the cover bag 23 in a state stored in the sensor bag 24. The sensor bag 24 and the air cells 21 are not fixed herein. Thus, the movement of the sensor main body 30 associated with the movement of the air cells 21 is prevented. Accordingly, body pressure distribution of a sleeper can be accurately detected regardless of the movement of the air cells 21.

Furthermore, it is easy to attach and detach the sensor bag 24 of the body position and pressure control apparatus 1 according to the present embodiment. Thus, it is easy to attach and detach the sensor main body 30 and the cushion mat 6. The sensor bag 24 is removed from the mattress 2 and the mattress 2 is folded, and thereby the body position and pressure control apparatus 1 can be stored and packed compactly. It is also easy to clean the mattress 2.

(Sixth Embodiment)

A body position and pressure control apparatus of the present embodiment is different from the body position and pressure control apparatus of the first embodiment in that a sensor holder is provided inside a mattress. Thus, only the difference is explained herein.

Figure 10:
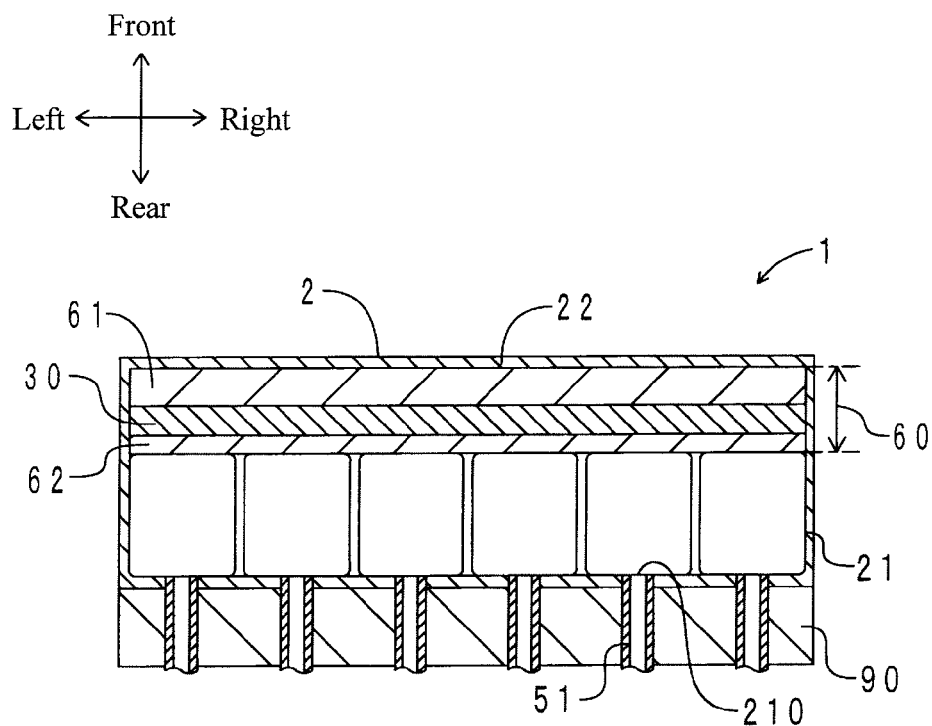
[FIG. 10] A cross-sectional view of a body position and pressure control apparatus according to a sixth embodiment.

FIG. 10 is a cross-sectional view of the body position and pressure control apparatus according to the present embodiment. FIG. 10 corresponds to FIG. 2. In FIG. 10, components corresponding to those in FIG. 2 are thus represented by the same reference numerals. As shown in FIG. 10, a body position and pressure control apparatus 1 of the present embodiment has a mattress 2 and a sensor holder 60.

The mattress 2 is provided with air cells 21 and a cover bag 22. The air cells 21 are stored inside the cover bag 22 and is disposed in a lower portion of the cover bag 22.

The sensor holder 60 is stored inside the cover bag 22 and is disposed on upper surfaces of the air cells 21. The sensor holder 60 and the air cells 21 are not fixed. The sensor holder 60 is provided with a sensor main body 30 and a pair of cushion mats 61 and 62. A configuration of the sensor main body 30 is identical to that in the first embodiment. The pair of cushion mats 61 and 62 are each composed of a three-dimensional fabric (same as above), such as polyethylene terephthalate and the like. The pair of cushion mats 61 and 62 are disposed on two sides in the thickness direction (vertical direction) of the sensor main body 30. The pair of cushion mats 61 and 62 are each bonded to a periphery of the sensor main body 30. An upper surface of the sensor holder 60 (upper surface of the upper cushion mat 61) is bonded to an internal surface of an upper skin of the cover bag 22. Thereby, the sensor holder 60 is fixed to the cover bag 22. In other words, the sensor main body 30 is fixed to the cover bag 22 through the cushion mat 61.

The body position and pressure control apparatus of the present embodiment has similar functions and effects to the body position and pressure control apparatus of the first embodiment with respect to the components having common configurations. In the body position and pressure control apparatus 1 of the present embodiment, the pair of cushion mats 61 and 62 are disposed on the two vertical sides of the sensor main body 30, thus improving breathability and cushioning capability. Furthermore, the cushion mat 62 is provided between the sensor main body 30 and the air cells 21. The sensor main body 30 is fixed to the cover bag 22 of the mattress 2 along with the cushion mats 61 and 62. Thus, the movement of the sensor main body 30 associated with the movement of the air cells 21 is prevented. Accordingly, body pressure distribution of a sleeper can be accurately detected regardless of the movement of the air cells 21.

(Seventh Embodiment)

A body position and pressure control apparatus of the present embodiment is different from the body position and pressure control apparatus of the sixth embodiment in that a sensor holder is provided inside a sensor bag. Thus, only the difference is explained herein.

Figure 11:
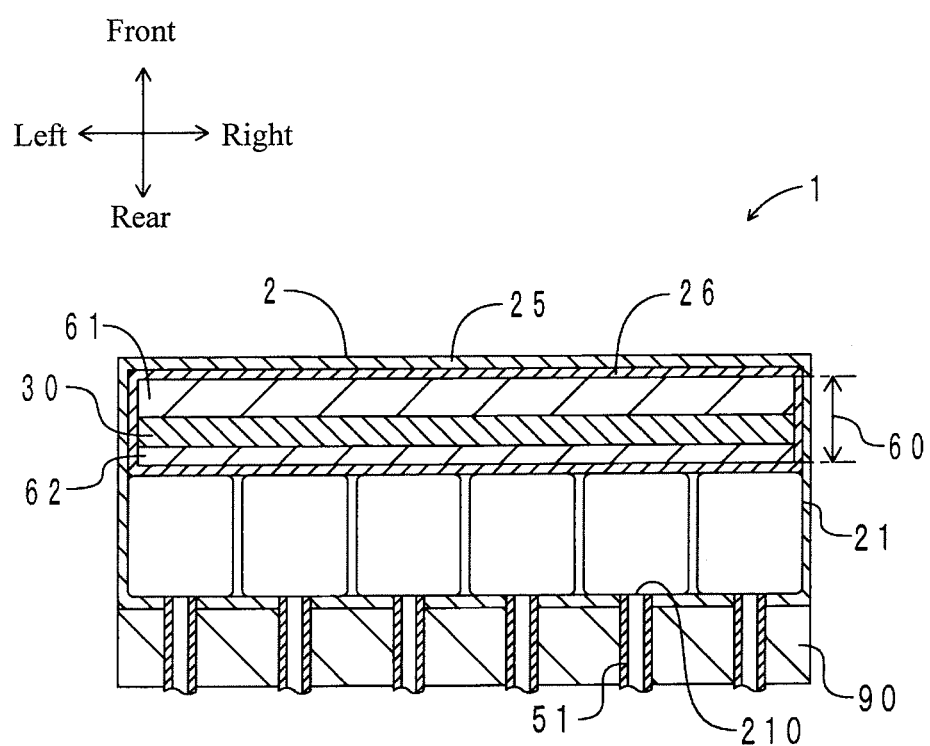
[FIG. 11] A cross-sectional view of a body position and pressure control apparatus according to a seventh embodiment.

FIG. 11 is a cross-sectional view of the body position and pressure control apparatus according to the present embodiment. FIG. 11 corresponds to FIG. 10. In FIG. 11, components corresponding to those in FIG. 10 are thus represented by the same reference numerals. As shown in FIG. 11, a body position and pressure control apparatus 1 of the present embodiment has a mattress 2, a sensor bag 26, and a sensor holder 60.

The mattress 2 is provided with air cells 21 and a cover bag 25. The air cells 21 are stored inside the cover bag 25 and is disposed in a lower portion of the cover bag 25. A plurality of hook-and-loop fasteners (not shown in the drawing) to attach a sensor bag 26 are provided along a periphery of an internal surface of an upper skin of the cover bag 25. The cover bag 25 is included in a cover member of the present invention.

The sensor bag 26 is stored inside the cover bag 25 and is disposed above the air cells 21. A plurality of hook-and-loop fasteners (not shown in the drawing) are provided along a periphery of an upper surface of the sensor bag 26. The hook-and-loop fasteners of the cover bag 25 and the hook-and-loop fasteners of the sensor bag 26 are engaged, and thereby the sensor bag 26 is detachably attached to the cover bag 25.

The sensor holder 60 is stored inside the sensor bag 26. The sensor holder 60 is fixed to the cover bag 25 through the sensor bag 26.

The body position and pressure control apparatus of the present embodiment has similar functions and effects to the body position and pressure control apparatus of the sixth embodiment with respect to the components having common configurations. In the body position and pressure control apparatus 1 of the present embodiment, the sensor holder 60 is fixed to the cover bag 25 in a state stored in the sensor bag 26. The sensor bag 26 and the air cells 21 are not fixed herein. Thus, the movement of the sensor main body 30 associated with the movement of the air cells 21 is prevented. Accordingly, body pressure distribution of a sleeper can be accurately detected regardless of the movement of the air cells 21.

Furthermore, it is easy to attach and detach the sensor bag 26 of the body position and pressure control apparatus 1 according to the present embodiment. Thus, it is easy to attach and detach the sensor main body 30 and the cushion mat 6. The sensor bag 26 is removed from the mattress 2 and the mattress 2 is folded, and thereby the body position and pressure control apparatus 1 can be stored and packed compactly. It is also easy to clean the mattress 2.

(Others)

The embodiments of the body position and pressure control apparatus according to the present invention are explained above. The present invention is not, however, particularly limited to the above embodiments. The present invention may be embodied in various modifications and improvements possibly performed by those skilled in the art.

As the sensor main body of the elastomer sensor, for example, an electrostatic capacitance sensor is used in the first and third through seventh embodiments, and a resistance increase sensor is used in the second embodiment. Thus, the configuration, shape, size and the like of the sensor main body are not particularly limited. The electricity output from the sensor main body may be in any one of voltage, electric resistance, electric capacitance, and the like.

An elastomer for the sensor thin film in the sensor main body is not limited to a specific type. For the elastomer sensor in the first and third through seventh embodiments, for instance, it is preferable to use an elastomer having high elongation, strength, and relative permittivity in view of enhancement in durability against repeated expansion and contraction and electrostatic capacitance. Examples of preferred materials may include a silicone rubber, an acrylonitrile-butadiene copolymer rubber, an acrylic rubber, an epichlorohydrin rubber, a chlorosulfonated polyethylene, a chlorinated polyethylene, a urethane rubber, a natural rubber, an isoprene rubber, foams of the above listed materials, and a urethane foam. For the elastomer sensor in the second embodiment, examples of preferred materials in view of compatibility with the conductive filler may include a silicone rubber, an ethylene-propylene copolymer rubber, a natural rubber, a styrene-butadiene copolymer rubber, an acrylonitrile-butadiene copolymer rubber, and an acrylic rubber. In the second embodiment, the electric resistance of the sensor thin film increases in accordance with an increase in the amount of elastic deformation (load). It is possible, however, to use a sensor thin film that decreases electric resistance in accordance with an increase in load. The behavior of the electric resistance of the sensor thin film can be adjusted by a type of an elastomer in the base material or a type and mixing ratio of the conductive filler.

An elastomer is included in the electrodes and wirings of the sensor main body in the first and third through seventh embodiments. In this case, there is an advantage in which the electrodes and wirings expand and contract, thus deforming along with the sensor thin film. The electrodes and wirings may be provided directly on the sensor thin film. Alternatively, the electrodes and wirings may be provided on a separate elastomer film in advance and the film may be laminated to the sensor thin film. In this case, examples of the elastomer film may include an elastomer, which is suitable for the sensor thin film as described above, a butyl rubber and an ethylene-propylene copolymer rubber, which have higher durability than the elastomer. The electrodes and wiring may be composed of a metal material or a material provided by metal plating a surface of an organic fiber. In any embodiment, the number and placement of the electrodes are not particularly limited. For the sensor main body in the first and third through seventh embodiments, for example, the number, width and length of the band-shaped front electrodes and rear electrodes may be determined appropriately. For instance, electrodes having wide and narrow widths may be mixed and placed. The number and placement of the detectors may be adjusted by changing the placement of the front electrodes and the rear electrodes.

One sensor main body is used to detect the body pressure distribution in the embodiments above. A plurality of sensor main bodies, however, may be used to detect the body pressure distribution. For example, a sensor main body densely provided with detectors and a sensor main body sparsely provided with detectors may be prepared separately. The former may be placed in a portion likely to cause bedsores and the latter may be placed in other portions.

The body pressure distribution of the whole body of the sleeper is detected in the embodiments above so as to distribute the body pressure and change the body position. However, the sensor main body may be placed only in a portion likely to cause bedsores to distribute the body pressure and change the body position.

The sensor main body is placed on the upper surface of the mattress in the first to third embodiments. The sensor main body, however, may be placed below the mattress or inside the mattress as in the fourth to seventh embodiments. In the first to third embodiments, the sensor main body and the mattress may be entirely bonded or not be bonded. In the case where the sensor main body is placed on the upper surface of the mattress as in the first to third embodiments, it is preferred that the sensor main body is not entirely bonded so that the sensor main body can easily follow the movement of the divided portions. In this case, the sensor main body can be prevented from being displaced, for example, by fixing a plurality of portions on the external edge of the sensor main body to the mattress.

In the fifth embodiment, the snap buttons are used to attach the sensor bag to the cover bag (cover member). In the seventh embodiment, the hook-and-loop fasteners are used to attach the sensor bag to the cover bag. A method of fixing the sensor bag, however, is not limited to the above. For instance, buttons may be provided to the sensor bag and button holes may be provided to the cover member. In this case, the sensor bag can be attached or detached by fastening or unfastening the buttons.

The cushion mat is placed on the upper surface of the sensor main body in the embodiments above. A material of the cushion mat is not limited as long as the material has breathability and cushioning capability. In addition to the embodiments above, a mat using a "Breathair (registered trademark)" of Toyobo Co., Ltd. may be used. Furthermore, no cushion mat may be placed. In the third embodiment in particular, the sensor main body is provided with the ventilation holes. It is thus hardly necessary to place a cushion mat in view of breathability, compared with the other embodiments. In the third embodiment, the ventilation holes are provided in the sensor thin film in portions where neither the front electrodes nor the rear electrodes are provided. The ventilation holes, however, may be provided in portions where the front electrodes or the rear electrodes are provided.

In the body position and pressure control apparatus, a cover may be placed to cover the upper most surface that contacts a sleeper, thus preventing the body position and pressure control apparatus, specifically, the cushion mat, the sensor main body, and the mattress from getting dirty, and improving the design. In this case, the cover is preferably breathable.

The mattress is composed of the cover bag and the plurality of divided portions (air cells) in the embodiments above. The mattress, however, is not limited to the structure in the embodiments above. The structure of the mattress may be determined appropriately according to a method of changing the body pressure distribution. For instance, the mattress itself may be a collection of a plurality of divided portions. In the case where the divided portions are bag portions, gas other than air or liquid such as water may be filled.

The divided portions of the mattress only have to be disposed so as to correspond to the detectors. It is not necessary, however, that the divided portions and the detectors are provided one to one. For example, two or more detectors may be disposed to one divided portion. Conversely, one detector may be disposed over two or more divided portions.

To change the body pressure distribution, a variety of methods may be employed in addition to supplying and exhausting fluid to the bag portions (divided portions) of the mattress to inflate and deflate the bag portions. For instance, actuators may be incorporated into the divided portions to vertically move the upper surfaces of the divided portions, the actuators each employing an electric-field responsive polymer, such as a dielectric elastomer. Alternatively, viscomagnetic fluid may be used to change the hardness of the divided portions.

The invention claimed is:

1. A body position and pressure control apparatus, comprising:
    a mattress comprising a plurality of divided portions and supporting a sleeper, and the mattress comprising a cover member covering the divided portions;
    an elastomer sensor comprising a sheet sensor main body and a calculator,
    the sensor main body being disposed one of above, below, and inside the mattress in a thickness direction thereof;
    the sensor main body comprising: an elastomer sensor thin film, a plurality of electrodes connected to the sensor thin film, and a plurality of detectors provided between the electrodes and corresponding to the divided portions, wherein the sensor main body is capable of outputting input load as electricity, and wherein the calculator calculates body pressure distribution of the sleeper from the output electricity;
    a body pressure adjuster controlling each of the divided portions based on body pressure distribution data detected by the elastomer sensor and thereby changing the body pressure distribution of the sleeper;
    a breathable cushion mat disposed closer to the sleeper than the divided portions; and
    a sensor bag attachably/detachably fixed inside the cover member, wherein the sensor main body and the cushion mat are stored in the sensor bag, wherein the sensor main body and the cushion mat are stacked in sequence on the sleeper side of the divided portions inside the cover member, and wherein the sensor main body and the cushion mat are fixed to the cover member.

2. The body position and pressure control apparatus according to claim 1, wherein
    the divided portions are composed of bag portions filled with one of gas and liquid, and
    the body pressure adjuster supplies one of the gas and the liquid to the bag portions to inflate the bag portions and alternatively exhausts one of the gas and the liquid from the bag portions to deflate the bag portions, and thereby changes the body pressure distribution of the sleeper.

3. The body position and pressure control apparatus according to claim 1, further comprising:
    a sensor holder comprising the sensor main body and the cushion mat defined by a pair of cushion mats fixed on two sides in a thickness direction of the sensor main body, wherein
    the sensor holder is disposed on the sleeper side of the divided portions inside the cover member, and
    the sensor holder is fixed to the cover member.

4. The body position and pressure control apparatus according to claim 3, further comprising:
    the sensor holder being stored in the sensor bag.

5. The body position and pressure control apparatus according to claim 1, wherein the sensor main body is provided with a plurality of ventilation holes penetrating in a thickness direction of the sensor thin film.

6. The body position and pressure control apparatus according to claim 1, wherein the divided portions are densely disposed in an area corresponding to a portion of the sleeper likely to cause bedsores.

7. The body position and pressure control apparatus according to claim 1, wherein the sensor main body has an elongation at break of 50% or greater.

8. The body position and pressure control apparatus according to claim 1, wherein, in the sensor main body, the electrodes comprises band-shaped front electrodes disposed on a front side of the sensor thin film and band-shaped rear electrodes disposed on a rear side of the sensor thin film, the front electrodes and the rear electrodes intersect viewed from a front-rear direction to form detectors, and electrostatic capacitance at the detectors is changed by input of the load.

9. The body position and pressure control apparatus according to claim 8, wherein the front electrodes and the rear electrodes comprise an elastomer and a conductive filler filled in the elastomer.

* * * * *